United States Patent
Eisenkraft et al.

(10) Patent No.: US 11,389,673 B2
(45) Date of Patent: Jul. 19, 2022

(54) SEALABLE MOUTHPIECE HAVING A HOLLOW DOME PORTION FOR USE IN CPR

(71) Applicant: DEA R&D LTD., Jerusalem (IL)

(72) Inventors: Arik Eisenkraft, Tel Mond (IL); Reuven Fichman, Modi'in-Macabim-Reut (IL); Asaf Yogev, Jerusalem (IL); Ariel Ben-Rey, Jerusalem (IL)

(73) Assignee: DEA R&D LTD., Jerusalem (IL)

( * ) Notice: Subject to any disclaimer, the term of this patent is extended or adjusted under 35 U.S.C. 154(b) by 474 days.

(21) Appl. No.: 15/536,263

(22) PCT Filed: Dec. 8, 2015

(86) PCT No.: PCT/IL2015/051188
§ 371 (c)(1),
(2) Date: Jun. 15, 2017

(87) PCT Pub. No.: WO2016/098099
PCT Pub. Date: Jun. 23, 2016

(65) Prior Publication Data
US 2018/0021606 A1   Jan. 25, 2018

Related U.S. Application Data

(60) Provisional application No. 62/092,285, filed on Dec. 16, 2014.

(51) Int. Cl.
*A62B 9/06* (2006.01)
*A61M 16/04* (2006.01)
(Continued)

(52) U.S. Cl.
CPC ........... *A62B 9/06* (2013.01); *A61M 16/0048* (2013.01); *A61M 16/0493* (2014.02);
(Continued)

(58) Field of Classification Search
CPC .......... A62B 9/06; A62B 9/04; A62B 18/025; A61M 15/0021; A61M 15/085;
(Continued)

(56) References Cited

U.S. PATENT DOCUMENTS 535,399 A * 3/1895 Pittman .................. D06F 55/00
24/533
670,306 A * 3/1901 Bering .................... D06F 55/00
24/551
(Continued)

FOREIGN PATENT DOCUMENTS

EP          0 845 277       11/2003
WO        WO-9933506 A1 *  7/1999  ........ A61M 16/0048

OTHER PUBLICATIONS

International Search Report for PCT/IL2015/051188 dated May 20, 2016.
(Continued)

*Primary Examiner* — Joseph D. Boecker
*Assistant Examiner* — Brian T Khong
(74) *Attorney, Agent, or Firm* — Nixon & Vanderhye PC

(57) ABSTRACT

An intraoral flexible mouthpiece including: a hollow dome portion including a peripheral proximal edge. The hollow dome portion extends distally, and the hollow dome portion includes a central orifice located at the distal portion of the hollow dome portion. A peripheral flexible sheet flange attached along the dome portion peripheral proximal edge. A tube attached to the central orifice and extending distally therefrom. The peripheral flexible sheet flange is configured to be placed in the mouth between the teeth and gums on one side and the lips and cheeks on the other side, and the hollow dome portion is configured to protrude distally out of the mouth.

20 Claims, 10 Drawing Sheets

(51) Int. Cl.
- A61M 16/06 (2006.01)
- A62B 18/02 (2006.01)
- A61M 16/00 (2006.01)
- A61M 16/20 (2006.01)

(52) U.S. Cl.
CPC .... A61M 16/0495 (2014.02); A61M 16/0616 (2014.02); A62B 18/025 (2013.01); A61M 16/20 (2013.01)

(58) Field of Classification Search
CPC .......... A61M 16/0616; A61M 16/0611; A61M 16/049; A61M 16/0488; A61M 16/0644; A61M 16/0048; A61M 16/20; A61M 16/0493; A61M 16/0497; G09B 23/288; A61B 17/1227; B42F 1/08; Y10T 24/44829; Y10T 24/44821; A61F 5/566; B63C 11/186; A63B 23/18
See application file for complete search history.

(56) References Cited

U.S. PATENT DOCUMENTS

| | | | | |
|---|---|---|---|---|
| 773,449 A * | 10/1904 | Anderson | ............... | D06F 55/00 24/533 |
| 1,070,202 A * | 8/1913 | Strange | ............... | D06F 55/00 24/549 |
| 2,521,084 A * | 9/1950 | Oberto | ............... | A61M 16/06 128/206.29 |
| 3,017,880 A * | 1/1962 | Brook | ............... | A61M 16/0048 128/203.11 |
| 3,126,002 A * | 3/1964 | Owens | ............... | A63B 71/085 128/861 |
| 3,139,088 A * | 6/1964 | Galleher, Jr. | ............... | A61M 16/0488 128/206.29 |
| 3,658,058 A * | 4/1972 | Neidhart | ............... | A61M 16/0488 128/201.18 |
| 4,169,473 A * | 10/1979 | Samelson | ............... | A61F 5/566 128/848 |
| 4,325,364 A * | 4/1982 | Evans | ............... | A62B 27/00 128/201.13 |
| 4,658,822 A * | 4/1987 | Kees, Jr. | ............... | A61B 17/1227 24/546 |
| 4,881,540 A * | 11/1989 | Vigilia | ............... | A61M 16/0048 128/202.28 |
| 5,174,284 A * | 12/1992 | Jackson | ............... | A61M 16/0488 128/200.26 |
| 6,088,889 A * | 7/2000 | Luther | ............... | A61B 17/1227 24/489 |
| 6,257,238 B1 * | 7/2001 | Meah | ............... | A61B 1/24 128/859 |
| 6,679,257 B1 * | 1/2004 | Robertson | ............... | A61M 16/0488 128/204.18 |
| 6,792,942 B1 * | 9/2004 | Ho | ............... | A61F 5/566 128/200.24 |
| 6,820,617 B2 * | 11/2004 | Robertson | ............... | A61M 16/08 128/204.18 |
| 6,981,502 B2 | 1/2006 | McCormick et al. | | |
| 2002/0069872 A1 * | 6/2002 | Gradon | ............... | A61M 16/0488 128/201.26 |
| 2002/0124844 A1 * | 9/2002 | Chiang | ............... | A62B 9/06 128/201.18 |
| 2003/0078139 A1 | 4/2003 | Norton | | |
| 2003/0089371 A1 * | 5/2003 | Robertson | ............... | A61M 16/0488 128/201.26 |
| 2003/0094177 A1 * | 5/2003 | Smith | ............... | A61M 16/06 128/204.18 |
| 2005/0217678 A1 * | 10/2005 | McCormick | ............... | A61M 16/06 128/206.29 |
| 2006/0206120 A1 * | 9/2006 | Clawson | ............... | A61C 19/05 606/151 |
| 2007/0251528 A1 | 11/2007 | Seitz et al. | | |
| 2008/0167676 A1 * | 7/2008 | Howard | ............... | A61F 5/56 606/199 |
| 2009/0056721 A1 * | 3/2009 | Leboeuf | ............... | A61M 16/0488 128/207.14 |

OTHER PUBLICATIONS

Written Opinion of the International Searching Authority issued in PCT/IL2015/051188 dated May 20, 2016.

* cited by examiner

FIG 1A
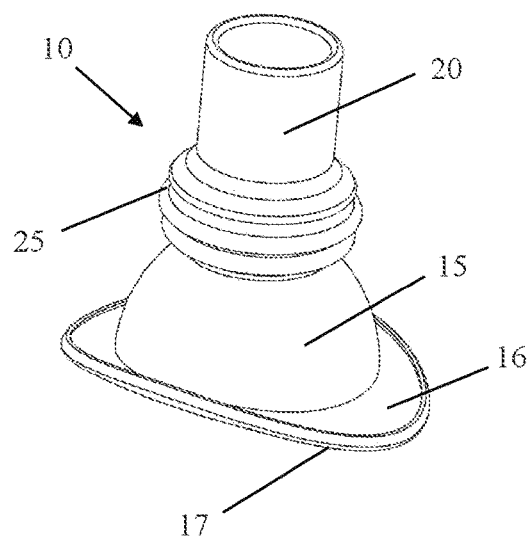
FIG 1B
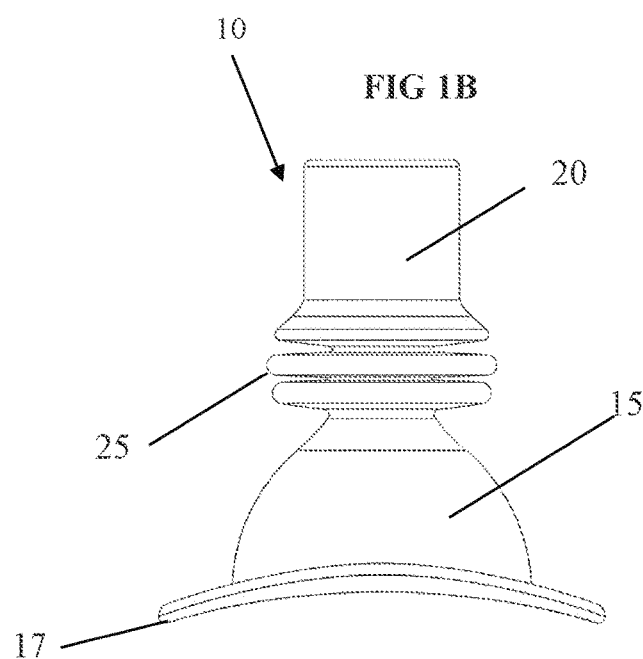
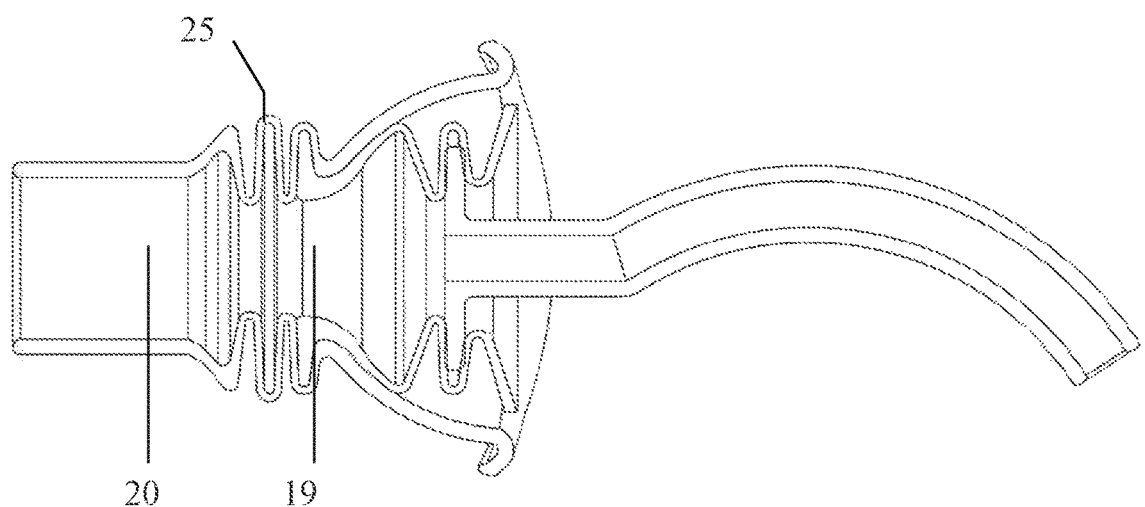
FIG 1C

FIG. 2A
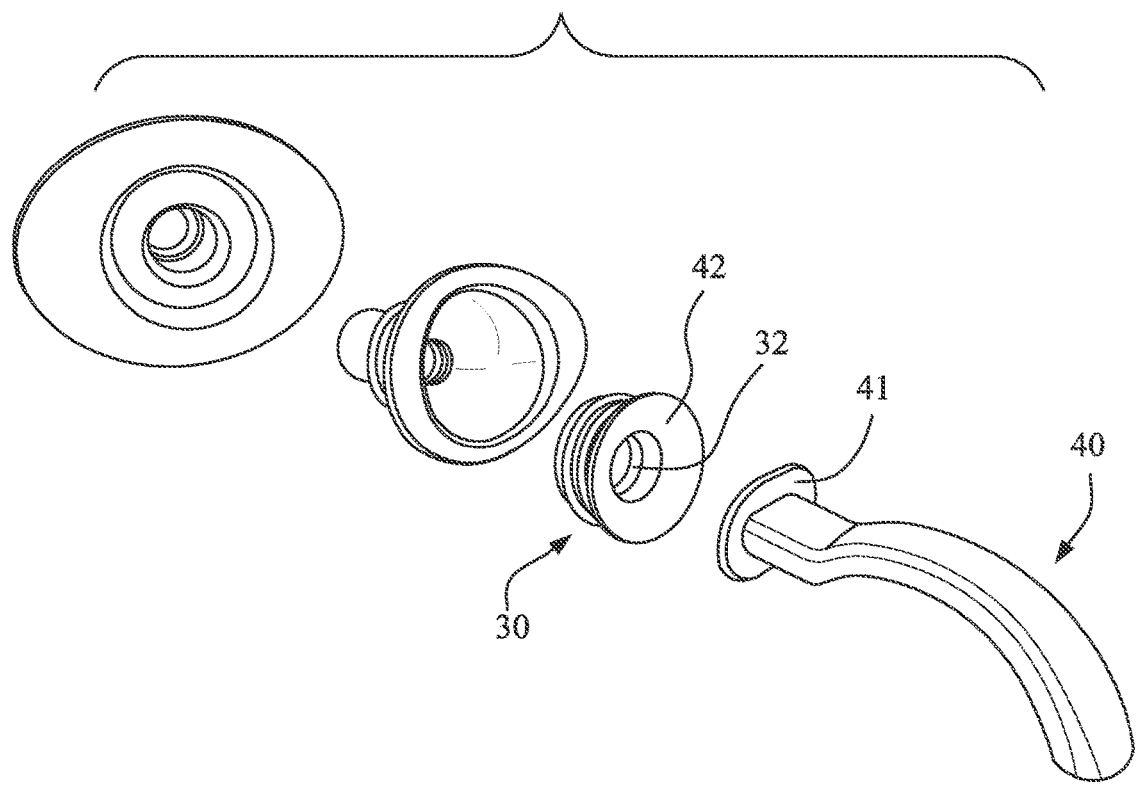
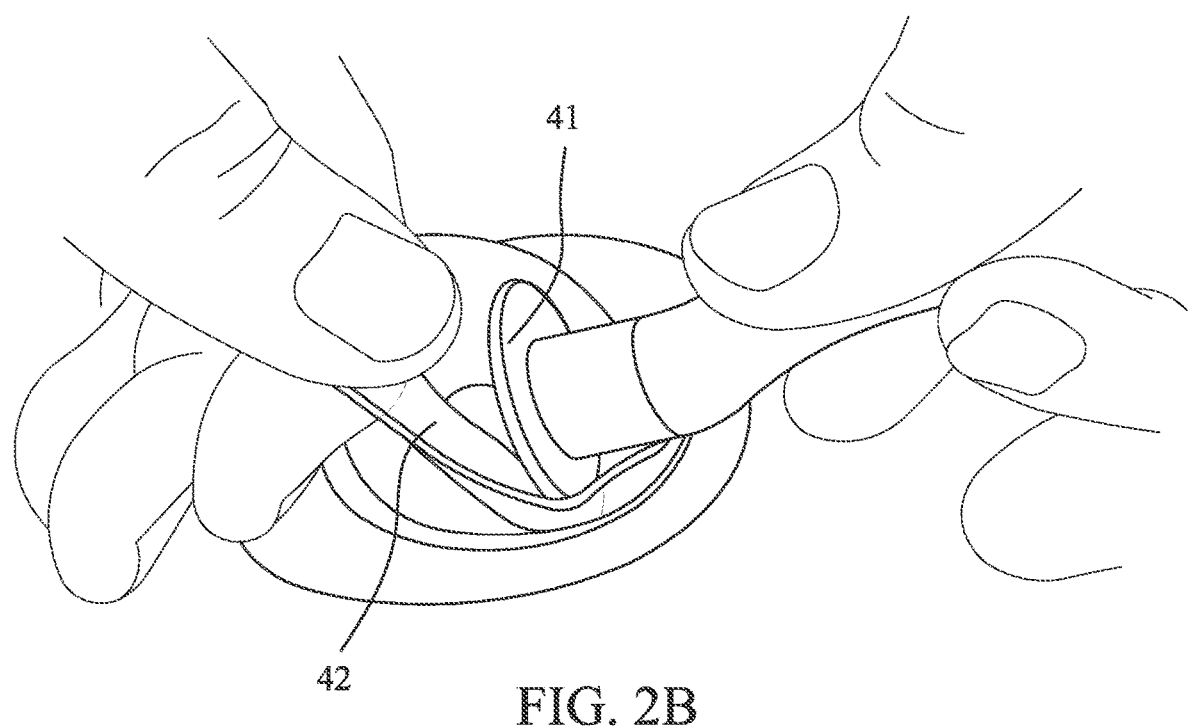
FIG. 2B

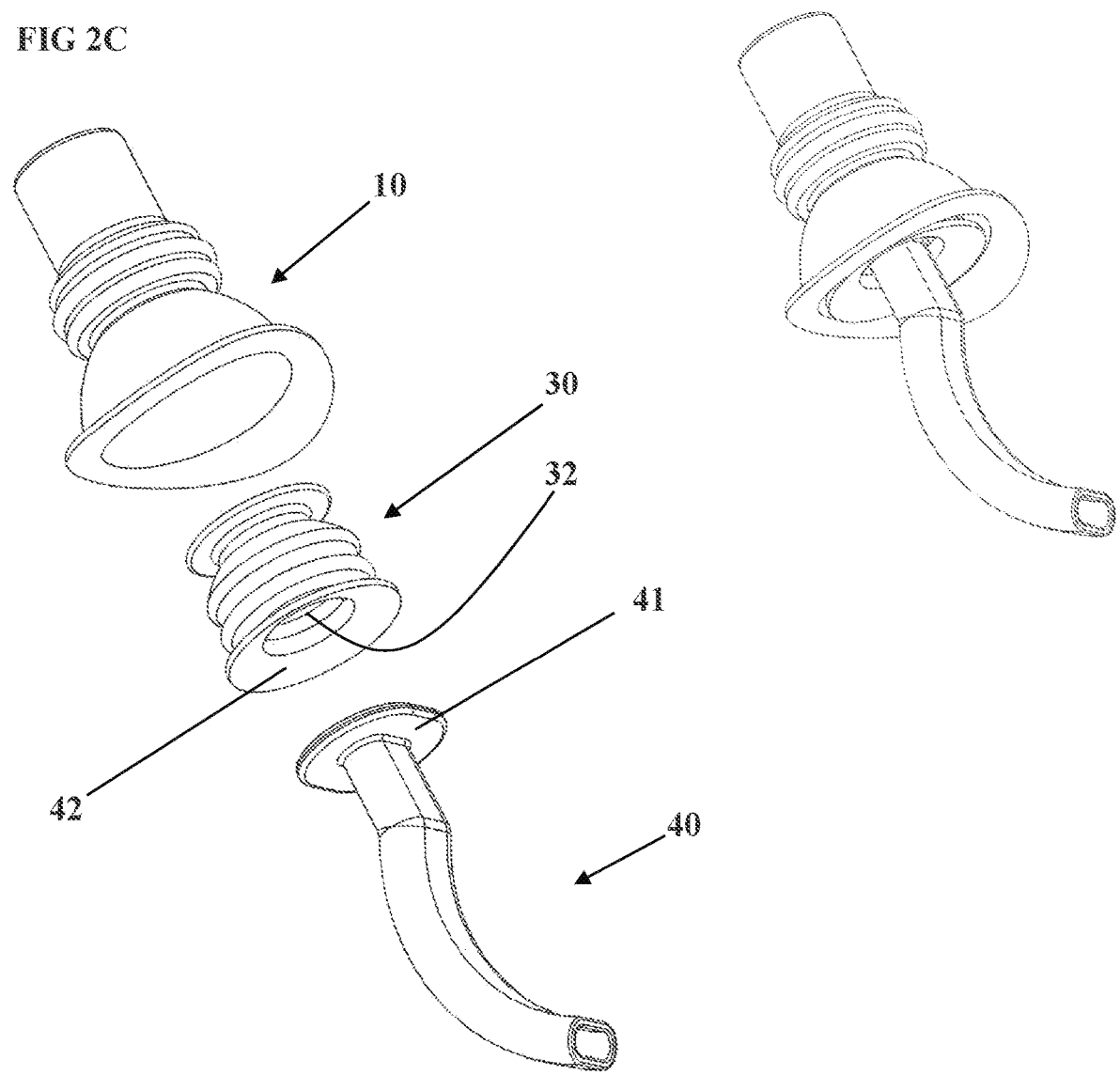

Length

Width

SEALABLE MOUTHPIECE HAVING A HOLLOW DOME PORTION FOR USE IN CPR

This application is the U.S. national phase of International Application No. PCT/IL2015/051188 filed Dec. 8, 2015 which designated the U.S. and claims the benefit of U.S. Provisional Application No. 62/092,285 filed Dec. 16, 2014, the entire contents of each of which are hereby incorporated by reference.

FIELD OF THE INVENTION

The present invention relates to the field of medical instruments and appliances. More particularly, the present invention relates to a sealable mouthpiece that enables ventilation without leakage.

BACKGROUND OF THE INVENTION

Respiratory masks are commonly used during emergency care e.g. to treat Cardiopulmonary Resuscitation (CPR). To carry out an effective treatment, means are provided for periodic air/gas delivery to the lungs of a patient and periodic appliance of heart massage techniques. Prior art methods and means have been provided for effective air/gas delivery to the lungs. These methods and means emphasize on providing sufficient air delivery means, avoiding blockage and enabling patency of the air delivery organs. Also these methods and means emphasize on providing means to avoid air leakage during delivery.

Devices commonly used for these purposes have several shortcomings. Dome/cup shaped mask devices that fit over the mouth and nose of a patient are prone to air leakage at its peripheral surface at uneven facial areas (e.g. nose bridge). Several size masks must be carried by first aid rescuer personnel so that an adequate size mask may be applied to each specific patient. Facial hair, vomit or blood coming out of wounds impedes on the mask sealing. Lips or teeth resistance impedes on the air flow delivery. Also, when pressure pressing the mask to the face some of the face portions are prone to injury and discomfort.

When a bag valve is used, it usually requires two healthcare providers, one for pressing the bag and inflating the air, and the other for pressing the mask against the patient's face to obtain a seal. However, it is not uncommon for only a single healthcare provider to attend a CPR incident. Moreover, in cases where more than one healthcare providers attend a CPR incident, there are many moments wherein a single healthcare provider actually attends the patient, while the others are busy calling for help, and preparing aid equipment such as IV tubing, or an AED device.

While the theoretical procedure of performing CPR is well defined and known to healthcare personnel, the practical execution of the CPR under field conditions is sometimes different. Various confusable complex situations may occur, e.g. while a single healthcare provider is positioned near the patient's head pressing the traditional mask to the patient's face with one hand, and performing chest compressions with the other hand.

Even when a single healthcare provider performs the correct treatment steps, using a traditional mask, he needs to waste precious time while swapping between applying chest compressions and air ventilation. With each swap from chest compressions to ventilation, the healthcare provider needs to grab the mask, adjust it on the patient's face to achieve maximum sealing, apply pressure on the face, and ventilate via either his own mouth or another gas source. Following the ventilation, the healthcare provider needs to place the mask somewhere (usually on the ground) before being available for chest compressions. The commonly advised medical procedure duration of this cycle (from chest compression to chest compression) is under 10 seconds in order to maintain a continuous blood flow by the chest compressions. These medical steps performed according to CPR guidelines while using a traditional mask are extremely time consuming, and demand a great deal of effort and accuracy in order to achieve ventilation and chest compression efficiency. Clearly there is a need to reduce these large numbers of steps/actions and their complexity.

In an attempt to overcome some of these shortcomings there have been attempts to provide efficient air delivery using mouthpieces in conjunction with additional intra-oral applications (e.g. bite blocks, flanges, seal bladders). Many of these solutions have several shortcomings when applied such as causing oral injuries, causing jaw fatigue and discomfort, incompatibility of the plurality of applications to accommodate typical oropharyngeal airways, etc.

U.S. Pat. No. 6,981,502 relates to a respiratory mask that functions with an intraoral mouthpiece in order to perform CPR. However, the mouthpiece disclosed therein does not achieve a full sealing outline. This situation requires for the healthcare provider to apply pressure and hand grip the mask to obtain a tight sealing. A poor grip may cause air leaks, leading to a stronger pressure application by the user, or alternatively, releasing the grip and repositioning/reapplying the hand for an improved grip. In addition, the patient's face may be covered fluids such as blood, emesis or sweat, creating a slippery surface, which leads the user to apply more pressure in order to maintain the sealing. Moreover, another disadvantage of the mask and mouthpiece of U.S. Pat. No. 6,981,502 applied with a gas source (such as a bag valve resuscitator) is the inability to keep the mouthpiece in place due to the gas source (connected to it) weight and leverage. Therefore the healthcare provider could actually be required to reapply the mouthpiece to the patient's mouth with each ventilation cycle. The inner section of mouthpieces for gas flow or resuscitation is typically placed parallel to the gums and teeth, and not pressured to them, therefore requiring and additional pressing feature (e.g. health provider's hand or reinforcing collar) for creating an efficient sealing.

EP 0845277 relates to a breathing assistance apparatus adapted to deliver gases to a patient and to assist said patient's breathing including gases supply means, including pressure regulating means adapted to supply gases at a required pressure level, means for providing an indication of the pressure of said gases, humidification means which receive said supplied gases and humidify said gases, said humidification means capable of variably humidifying said gases up to a required humidity level, humidified gases transportation pathway means which channel said humidified gases to said patient, means for providing an indication of the humidity of said gases. The breathing assistance apparatus is used in the treatment of Obstructive Sleep Apnea and also comprises a mouthpiece means adapted to be worn by the patient in the region of the mouth.

The prior art methods still lack efficient means for executing an efficient CPR procedure that overcome several of the aforementioned shortcomings. It is therefore an object of the present invention to provide a method and means to overcome the aforementioned shortcomings.

It is an object of the present invention to provide a method and means for efficiently sealing the mask/mouthpiece to the patient and enable efficient air delivery.

Other objects and advantages of the present invention will become apparent as the description proceeds.

SUMMARY OF THE INVENTION

The present invention relates to a flexible mouthpiece for use in CPR treatment. The mouthpiece is fit for use with various patients having various mouth dimensions. The mouthpiece comprises a hollow dome shaped flexible portion in its center. A flexible strap sheet is attached to, and surrounds the dome shaped portion proximal edge (in a sealed manner). The mouthpiece is configured to be placed in a patient's mouth wherein the flexible strap sheet is configured to be placed between the teeth and gums on one side of the sheet and the lips and cheeks on the other side. The lips are configured to contact the dome shaped portion, wherein the dome shaped portion protrudes out of the mouth distally. The proximal direction is herein defined as the direction towards the inner side of the mouthpiece, towards the patient throat, and the distal direction is herein defined as the direction towards the outer side of the mouth piece, away from the patient (when the mouthpiece is applied). These directions also apply to additional elements attached/coupled to the mouthpiece.

The dome shaped portion keeps the lips contacting it in an open and tightened state, thus causing a tight seal for inflation fluid to travel through the mouthpiece without leaking out. The dome shaped portion distal end comprises an orifice/hole. A tube (preferably flexible) extends distally from said orifice/hole circumference in a manner that a sealed passage way is formed from the inside of the tube to the orifice/hole. The tube is configured to connect to inflation means such as an ambu or bag valve resuscitator. The tube preferably comprises a corrugated portion that assists in maintaining the sealing when the inflation means is moved around during the CPR process. Optionally a corrugated portion can be sealably attached between a tube at its distal side and the orifice/hole circumference at its proximal side (in a sealable manner).

According to a preferred embodiment the mouthpiece further comprises a flexible corrugated conduit that extends from the orifice/hole circumference proximally (within the dome shaped portion) in a manner that a sealed passage way is formed from the orifice/hole to the inside of the flexible corrugated conduit. The flexible corrugated conduit is configured to sealably connect to a flange of an oropharyngeal airway. The flange of the oropharyngeal airway is placed within the flexible corrugated conduit (within one of the channel like portions that make the corrugations). The flange stretches said channels causing the channels to tightly surround the flange circumference causing a tight seal. Flanges of many sizes can be inserted into the channel due to the flexibility of the flexible corrugated conduit.

According to one embodiment, the mouthpiece comprises a proximal flange configured to be placed in the mouth between the teeth and gums on one side and the lips and cheeks on the other side, and a distal flange configured to be placed distally to the lips, wherein said distal flange is attached around a peripheral portion of the dome portion, that is distal to the dome portion proximal peripheral edge.

The present invention relates to an intraoral flexible mouthpiece comprising:

a hollow dome portion comprising a peripheral proximal edge wherein said hollow dome portion extends distally and wherein said hollow dome portion comprises a central orifice located at the distal portion of said hollow dome portion;

a peripheral flexible sheet flange attached along said dome portion peripheral proximal edge;

a tube attached to said central orifice and extending distally therefrom;

wherein said peripheral flexible sheet flange is configured to be placed in the mouth between the teeth and gums on one side and the lips and cheeks on the other side, and wherein the hollow dome portion is configured to protrude distally out of the mouth.

Preferably, the mouthpiece tube is flexible.

Preferably, the mouthpiece tube comprises a resilient portion (which is preferably a corrugated portion).

Preferably, the mouthpiece flange comprises an edge surrounding said flange, wherein said flange edge is curved and/or comprises a thickened portion.

Preferably, the mouthpiece flange is configured to be substantially parallel to the teeth of a user.

Preferably, the mouthpiece further comprises a flexible corrugated conduit having a distal end and a proximal end wherein said corrugated conduit distal end is attached to the orifice from withinside said dome portion (from the inside of the dome portion).

Preferably, the mouthpiece proximal end of the flexible corrugated conduit comprises a grip handle.

Preferably, the mouthpiece further comprises a distal flange configured to be placed distally to the lips, wherein said distal flange is attached around a peripheral portion of the dome portion, that is distal to the dome portion proximal peripheral edge.

Preferably, the mouthpiece comprises a nose clamp attached thereto.

Preferably, the mouthpiece further comprises a strap connected at its first end to a nose clamp and at its second end to a ring portion configured to encircle a portion of the corrugated portion.

Preferably, the nose clamp comprises two flaps and a reinforcement member comprising a spring force feature that tends to apply pressure on said flaps pushing said flaps one towards the other.

Preferably, the nose clamp comprises two finger grips attached to the two flaps respectively, wherein said two finger grips are attached to the reinforcement member therebetween.

Preferably, the nose clamp comprises two longitudinal arms and a reinforcement member connected therebetween comprising a spring force feature that tends to apply pressure on said arms pushing said arms one towards the other.

Preferably, the nose clamp comprises two curved handles extending distally from the edges of the arms.

Preferably, the curved handles have a "U" shape such that they comprise edge portions that are substantially parallel to the arms.

The present invention relates to a system for applying CPR comprising:

the mouthpiece as described herein;

inflation means coupled to the mouthpiece tube.

The present invention relates to a system for applying CPR comprising:

the mouthpiece with the corrugated conduit;

wherein said system further comprises an oropharyngeal airway comprising a flange, a main body portion and a proximal tip, wherein said airway flange is adapted to sealably connect to the corrugated conduit.

Preferably, the aforementioned system with the mouthpiece with the corrugated conduit further comprises inflation means coupled to the mouthpiece tube.

The present invention relates to a method for treating an unconscious patient (e.g. a patient who is in cardiac arrest) comprising:
  a) inserting the mouthpiece as described herein into a patient's mouth;
  b) connecting the tube to inflation means;
  c) applying CPR using the inflation means.

The present invention relates to a method for treating an unconscious patient comprising:
  a) connecting the corrugated conduit of the mouthpiece (as described herein with the corrugated conduit) to an oropharyngeal airway flange;
  b) inserting and fitting the oropharyngeal airway (which its flange is connected to the corrugated conduit) into the patient;
  c) inserting said mouthpiece into a patient's mouth.
  d) connecting the tube to inflation means.
  e) applying CPR using the inflation means.

BRIEF DESCRIPTION OF THE DRAWINGS

The present invention is illustrated by way of example in the accompanying drawings, in which similar references consistently indicate similar elements and in which:

FIGS. 1A-1C illustrates a mouthpiece according to an embodiment of the present invention.

FIGS. 2A-2B are pictorial examples of another embodiment of the present invention with an inner corrugated conduit portion.

FIGS. 2C-2D illustrate examples of the embodiment of FIGS. 2A-2B.

FIGS. 6A-6E illustrate another embodiment of a nose clamp.

DETAILED DESCRIPTION OF THE INVENTION

Figure 1D:
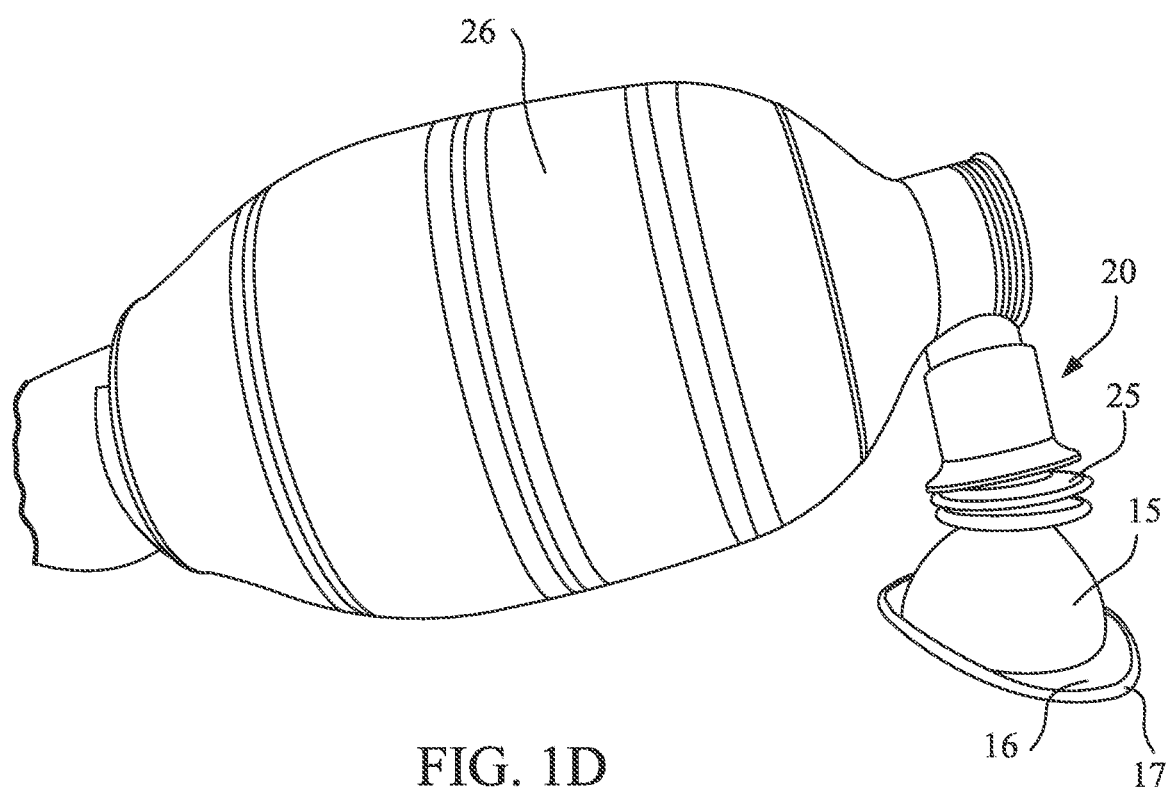
FIG. 1D is a pictorial example of the use of an embodiment of the present invention.

The present invention provides means that enable efficient treatment of CPR cases such that a single healthcare provider can treat a patient. Also, the air inflation can be sufficiently executed with the use of only one hand. An effective seal is obtained between the inflation means and the treated patient without the need of external support such as a healthcare provider's hand applying pressure to the mask. Also, the present invention insertion time is executed in a fast manner, and the seal is obtained in a shorter time than in typical prior art methods.

The present invention comprises an intraoral flexible mouthpiece 10 with a dome shaped portion 15, as shown in FIGS. 1A-1B. The present invention is capable of providing a one sized flexible universal component, which is adapted to fit a large portion of the population and eliminates the need to carry several mask sizes. The mouthpiece 10 is adapted to fit on patients with various facial features. The mouthpiece 10 unique hollow dome portion 15 protrudes outwardly out of the mouth and a peripheral strap sheet portion—flange 16 is attached to (along) the dome peripheral proximal edge. The proximal direction is herein defined as the inner side of the mouthpiece, towards the patient throat, and the distal direction is herein defined as the outer side of the mouth piece, away from the patient (when the mouthpiece is applied). These directions also apply to additional elements attached/coupled to mouthpiece 10.

According to an embodiment of the present invention, the peripheral flange 16 is adapted to be placed in the mouth along the gum line and is fixed in place between the lips/cheeks on one side and the gums/teeth on the other side of the person to be ventilated, preferably in a direction parallel to the teeth, wherein the dome shaped portion protrudes outwardly in a distal direction. The mouthpiece 10 does not require accurate alignment with the user's teeth or the user's palate to provide correct function and retention within the patient's mouth. The present invention also enables full efficiency and functionality within edentulous patients. The peripheral flange 16 is typically round and preferably oval/elliptic. This allows insertion of the mouthpiece 10 into the patient's mouth while manipulating it more easily. Optionally flange 16 comprises a bowed or saddle like shape.

The dome portion 15 comprises a central orifice 19 shown in cross section drawing FIG. 1C. The central orifice 19 is located at the peak/maximum distal portion of dome 15. A flexible tube 20 is attached to central orifice 19 and is configured to sealably couple it to inflation means. Flexible tube 20 preferably comprises a resilient portion. According to a preferred embodiment of the present invention, the resilient portion is a corrugated (pleat like/accordion like) portion 25. Optionally, the corrugated portion 25 is placed at the proximal end of tube 20 which is the portion attached to dome 15. Preferably corrugated portion 25 is attached to dome 15 with the assistance of a rigid safety ring to secure the connection.

Flexible tube 20 is coupled to a standard gas source (bag valve resuscitator), or other respiratory barrier device assisting in ventilation, supplying a mixture of gases used for ventilation. Preferably, the connection of the gas source to the flexible tube 20 is such that the gas source comprises a tube coaxial with tube 20 wherein the inner tube is tightly pressed against the outer tube. Optionally, the health care provider can put his lips around the distal end of tube 20 to ventilate directly air from his lungs. FIG. 1D shows an example of a bag valve resuscitator 26 (comprising a one way valve, as known in the art) coupled to tube 20.

The corrugated portion 25 allows flexibility between the gas source and the mouthpiece without interfering with the inflation taking place therebetween. Thus, it significantly reduces the forces applied on the mouthpiece by the connection means to the gas source, preventing the mouthpiece 10 from dislodging the mouth as a result of handling and manipulating the gas source. In prior art devices, the weight of the gas source and its manipulation may influence dislodging of a mouthpiece (connected to it) from the mouth of the patient. The present invention corrugated portion 25 allows moving the gas source distally and proximally from the mouth piece while it remains connected. It also allows angular motion of the gas source, placing the gas source on the floor or on the patient body (e.g. chest or neck), dynamic hand motion when operating the gas source, while mouthpiece 10 stays in place and maintains being sealed.

The present invention structure together with the natural behavior of the lips (i.e. applying an inward force when stretched outwardly), create a full sealing for air inflation necessary for artificial respiration. The present invention mouthpiece is configured to take advantage of two main natural seals that naturally exist when applying the mouthpiece to the mouth.

The flange 16 is placed between the gums and the inside of the lips. The flange edge 17 presses outwardly against the connection lines of the gums and upper portion of the lips and provide an efficient seal.

The outside (distal) surface of the dome 15 contacts the lips, thus creating a second and large area of peripheral sealing.

The dome shape naturally applying an outward force stretching the lips outwards keeps the lips in an open state. The lips natural flexibility, when being stretched tend to contract, thus pressing against the dome outside surface causing an efficient sealing. Also, the dome shape keeping the mouth opened causes an outward force on the flange edge 17 which outward force is applied on the connection lines of the gums and upper portion of the lips. All this along with the mouth which tends to close, provide an efficient sealing. Thus there is no need to create an external sealing pressure (e.g. pressing the mouthpiece with the health provider's hand) to achieve a complete sealing. Prior art mouthpieces without the dome effect are usually mostly parallel to the teeth and gums, thus requiring an additional factor (e.g. a handgrip or an additional object/shield) to ensure the pressure application between the lips and the mouthpiece to obtain sealing. In the present invention there is no need for an additional sealing factor. The present invention does not at all require a sealing connection to the surface of a face of a patient.

According to an embodiment of the present invention, the outer flange edge 17 is curved and/or thickened, thus providing an even more efficient sealing. The combination of the flanged mouthpiece location (between the lips and the gums), and the curved and thickened flange edge 17 create a pressurized seal. The curved flange edge 17 in combination with the thickened edge 17 and the flange size create an undercut which prevents the mouthpiece from an undesirable dislodging of the mouth.

The present invention, not requiring an external handgrip for sealage and for keeping in place, enables the hands of the healthcare provider to be free to manage/operate the gas source (such as a bag valve resuscitator) and to execute other vital CPR treatments. This also reduces complexity and reduces the number of CPR treatment actions. The present invention also enables a direct airflow from the gas source (e.g. bag valve/ambu) to the pharynx, overcoming obstacles existing in prior art devices such as lips and teeth resistance, and enables a direct route/airflow without having air leaks. Thus the present invention obtains maximum exploitation of the air pressure and prevents waste of the air pressure applied, and actually prevents waste of the efforts to produce the air pressure.

Also, it is not required that an external shield or restraining straps, keep the mouthpiece in place. Using an external shield or restraining straps, although provide a long lasting solution for achieving sealing without user fatigue, however, applying it is time consuming which can be extremely dangerous in CPR cases, wherein every moment could affect the final outcome. Prior art methods that use a handgrip to maintain sealing, although quick and available, leads to user fatigue, whether applying pressure on the patient's face or applying pressure while fastening the hand to the mask/mouthpiece or nose. In addition, a single handed hand grip directly on the face of the patient may cause sweaty palms, leading to a slippery surface, requiring the user to repeatedly improve his handgrip, therefore distracting the user from his main objective. On the other hand, in the present invention, after applying and correctly placing the mouthpiece and the nose clamp, both hands are free to carry out a proper and efficient artificial respiration, as well as rapid swapping between artificial respiration and chest compressions. All this is accomplished with a single healthcare provider, a more convenient solution for a long term operation.

According to an embodiment of the present invention, the mouthpiece comprises ear straps, preferably attached to the dome portion of the mouthpiece, to be hooked around the ears for additional support. This provides additional pressure and further contributes to prevent the mouthpiece from dislodging out of the mouth.

According to an embodiment of the present invention, the mouthpiece can act as a supplement to an already inserted oropharyngeal airway due to its flexibility and spring abilities to "squash" and therefore maintain pressure on the oropharyngeal airway flange—thus, creating a pressurized sealing. Thus the inflated air travels from the inflation means to the tube 20 through orifice 19 through the airway opening surrounded by the airway flange and into the patient's throat (pharynx).

The intraoral mouthpiece 10 and tube 20 of the present invention comprise one or more of the following materials—plastic, rubber, silicon, Latex. Alternatively, mouthpiece 10 and tube 20 may comprise other flexible/resilient suitable materials.

The diameter of the dome portion 15 is usually between 15 mm and 40 mm and preferably 22 mm. Its height is usually between 10 mm and 50 mm and preferably 28 mm. Its thickness is usually between 1 mm and 6 mm and preferably 2 mm.

The width of the flange portion 16 (including portion 17) is usually between 40 mm and 80 mm and preferably 56 mm. Its length is usually between 55 mm and 90 mm and preferably 72 mm. Its thickness is usually between 1 mm and 6 mm and preferably 2 mm. The height of the thickened flange edge 17 (from the edge surface of flange 16) is usually between 0.1 mm and 4 mm and preferably 0.9 mm.

The diameter of the corrugated portion 25 is usually between 27 mm and 47 mm and preferably 37 mm. Its length in a rested state is usually between 12 mm and 36 mm and preferably 18 mm. Its thickness is usually between 0.5 mm and 4 mm and preferably 1 mm. The distance between the outer edges of the parallel flexible segments (the length of each pleat/channel section) is usually between 4 mm and 12 mm and preferably 5 mm.

The diameter of the tube portion 20 is usually between 20 mm and 30 mm and preferably 25 mm. Its length (not including portion 25) is usually between 20 mm and 30 mm and preferably 23 mm. Its thickness is usually between 1 mm and 5 mm and preferably 2 mm.

FIGS. 2A-2D show a preferred embodiment of the present invention. According to this preferred embodiment, the mouthpiece 10 comprises an internal flexible, resilient and corrugated (pleat like/accordion like) conduit connector portion, hereinafter referred to as conduit 30, which its distal end is configured to be sealably coupled/attached to the orifice 19 from withinside the dome 15. The corrugated conduit 30 comprises a plurality of adjacent channels which actually form the corrugations. Optionally, the conduit 30 can connect to a more proximal portion of the inner side of dome 15 in relation to orifice 19, but still maintaining a complete closure sealing in a manner that inflation of air will fully travel from orifice 19 through conduit 30 without air leakage. Conduit 30 is configured to connect to an oropharyngeal airway at a more proximal location. Conduit 30 is compatible to sealably connect to a wide range of oropharyngeal airways, diverse in shape and size in order to obtain a sealed transfer of gas from the gas source to the pharynx. In some cases, the sealage is obtained even in cases where the patient suffers from jaw spasm.

As known in the art, oropharyngeal airways have three main portions: a flange, a main body portion and a proximal tip. The flange is the distal portion that usually protrudes from the mouth and rests against the lips/teeth, preventing the device from sinking into the pharynx. The body portion follows the contour of the roof of the mouth, and curves over and rests on top of the tongue. The proximal tip, sits at the base of the tongue.

FIGS. 2A-2D show airway 40 comprising distal flange 41, which is configured to fit within the inner portion of corrugated conduit 30. Due to the accordion like structure of conduit 30, it actually defines parallel interior channels 32 along its length, situated in a perpendicular direction to its length. The parallel channels 32 situate on the peripheral circumference of conduit 30 and each channel 32 completes a full circumferential rotation. The airway flange 41 is placed within one of the channels 32 and is fixed thereto between the channel sides. The conduit 30 (and channels 32) is preferably round, circular or elliptic. Preferably, the airway flange 41 is placed within the most proximal channel 32.

Conduit 30 is located within dome 15 wherein the flange 41 is placed in channel 32. Airways of many sizes can be used with the present invention. Various flange sizes can be inserted into conduit 30 wherein the airtight sealing is obtained even when using several flange sizes. The flange 41 can be inserted into the best located channel to be positioned against the teeth. The conduit 30 being flexible enables the sealing, such that the flange 41 inserted into channel 32 stretches the channel 32 flexible material creating a close tight air seal. When a large flange 41 is used it substantially stretches the channel material creating an even more tight efficient seal. FIG. 2D shows the insertion of the flange 41 into the conduit 30 by stretching flexible channel 32 before it contracts and forms the sealing. FIG. 1C shows a cross-section of the mouthpiece and the corrugated conduit and the airway inserted therein can also be seen.

The most proximal portion of conduit 30 acts as a "grip handle" 42 and enables the medical personnel to grip the conduit 30 with one hand and insert the flange 41 into the channel 32 with the other hand, as shown in FIG. 2D. FIG. 2D. shows a user holding the grip handle 42 at one side and inserting flange 41 near the other side. The grip handle 42 can be wider (with a larger diameter) and/or thicker than the central portions of the conduit 30. Flexible channel 32 contracts on flange 41 causing an efficient seal and a firm grip that prevents the airway 40 from dislodging and the air from leaking out. Thus the inflated air travels from the inflation means to the tube 20 through orifice 19 through the flexible channel 32 through the airway opening surrounded by the airway flange 41 and into the patient's throat (pharynx). The sealing mentioned herein prevents leakage of the inflated air.

According to a preferred embodiment, when a healthcare provider arrives on the scene for treating a patient, he first connects an appropriate airway to the mouthpiece by insertion of the airway flange 41 into an appropriate channel of conduit 30. Then he correctly places the airway within the patient's mouth and throat thus keeping an open air path. The airway flange 41 (within channel 32) is placed distal to the teeth or distal to the lips. Then the attached mouthpiece 10 is inserted into the mouth such that the flange edges 17 contact the gums and the upper lips/cheeks. The lips edges contact the outer dome portion 15 beyond the outer/distal side of flange 16. The lips remain partially opened and stretched causing an efficient sealing. The distal portion of tube 20 is connected to inflation means (e.g. air bag), thus the inflation may commence. When using an air bag, when the healthcare provider wants to cease air inflation and start heart compressions he quickly places the airbag on the chest of the patient or on the floor and treats the heart. The corrugated portion 25 of tube 20 provides the ability to do so without dislodging the mouthpiece from the mouth or the airbag from tube 20. When the healthcare provider wants to inflate air again, he does not need to reapply the mouthpiece or apply pressure to the mouthpiece. He can just start inflating because the mouthpiece and all the elements connected thereto stay in place ready for use.

An important advantage of the present invention is the fact that the dome provides enough space to contain the corrugated conduit 30. The hollow space (actually out of the mouth distal to the lips) enables to contain the corrugated conduit 30 within it. Thus the mouthpiece can function well in combination with the airway, and without forming an interrupting presence inside the oral cavity.

In prior art cases where a mouthpiece is ridged, its immediate removal would require that a healthcare provider actively manipulate the patient's lips in order for the mouthpiece to be removed from the mouth. An instinct removal by the patient would not necessarily be possible. On the other hand, the present invention flexible mouthpiece 10, in cases where the patient awakens during the process and gags out the oropharyngeal airway, the patient would be able to instinctively remove the flange 16 out of the mouth easily by opening his mouth and coughing out the mouthpiece (or pushing it with his tongue). The flexibility of the mouthpiece enables the ejection of the airway while coughed out by an awakened patient, and will not disturb the patient's active respiration, when awakened.

Due to various facial structure differences (e.g. jaws, teeth, gums) between various people, the flexibility of mouthpiece flange 16 and corrugated conduit 30 contribute to the sealable functionality and compatibility of the present invention to the various facial structures and sizes. The present invention flexible mouthpiece can fit people with large and also small facial structures. Healthcare providers do not need to carry several present invention mouthpieces of various sizes to ventilate people of various ages and sizes. One flexible mouthpiece could be sufficient for various sizes. FIGS. 2A and 2C (pictorial and drawing respectively) illustrate the mouthpiece 10, the corrugated conduit 30 and the airway 40 separately (wherein in fact the distal portion of the corrugated conduit 30 is attached to the inner part of the dome as explained herein). FIG. 2D illustrates the components interconnected.

The air flow travels from the gas source 26 through tube 20 and mouthpiece 10 through airway 40 to the throat and lungs. The Air exits the lungs to the throat and through the airway 40, mouthpiece 10, tube 20, and out to the open air via a one way valve placed on the edge of the gas source 26.

Conduit 30 comprises one or more of the following materials—plastic, rubber, silicon, Latex. Alternatively, it may comprise other flexible/resilient suitable materials. The diameter of the conduit 30 is usually between 8 mm and 50 mm and preferably 35 mm. Its length (in a rested state) is usually between 5 mm and 40 mm and preferably 22 mm. Its thickness is usually between 0.1 mm and 4 mm and preferably 1 mm. The distance between the outer edges of the parallel flexible segments (the length of each pleat section comprising channel 32) is usually between 1 mm and 12 mm and preferably 5 mm.

Achieving complete sealing during the whole CPR process is essential for a proper artificial respiration because of the increased pressure created inside the mouth during ventilation. In addition, the mouthpiece needs to maintain sealing while addressing 2 possible conditions of the person to be ventilated—complete relaxation of the jaw, or spasm. Therefore, these conditions combined with the high pressure strongly require a well based sealing that could withstand these different conditions without any manual or external pressure added. The present invention provides the necessary sealing.

The present invention portions (e.g. dome 10, tube 20, flange 16, conduit 30,) may be manufactured and formed together as a unified cast structure or may be attached together by welding, sticking, pasting, gluing, stitching, sewing, or by other methods known in the art.

According to another embodiment of the present invention, the mouthpiece comprises an additional flange for increased sealing. FIGS. 3A-3D illustrate a mouthpiece 110 comprising a proximal flange 16a and a distal flange 16b wherein the lips are configured to be placed between said flanges. A channel 18 is formed bounded by the flanges 16a and 16b and the dome portion that they are attached to. The proximal flange 16a is at the most proximal portion of the mouthpiece 110 and is adapted to be placed in the mouth extending the gum line and is fixed in place between the lips and the gums and cheeks of the person to be ventilated (in similarity to flange 16 described hereinabove). The distal flange 16b is adapted to be placed distally to the lips. The distance between the flanges 16a and 16b is such that the lips placed therebetween can be fit therein wherein both flanges press the lips causing an increased sealing. The distal flange 16b is attached around a peripheral portion of dome portion 115 that is distal to the dome portion 115 proximal peripheral edge. The dome shape of dome portion 115 causes the lips to be stretched and with both flanges pressing the lips the increased sealing is achieved.

The flanges are comprised of the same materials (and optionally similar sizes) as explained herein regarding flange 16. Optionally the flanges 16a and 16b comprise outer flange edges 17a and 17b (respectively) are curved and/or thickened (in similarity to flange edge 17 described hereinabove). Preferably, the flanges 16a and 16b comprise a round or elliptic or oval or bowed or saddle like shape. The shape of the dome 10 connected to the flanges 16a and 16b is adapted accordingly. Optionally, the curved arc of flange 16a adapted to be placed aside the lips comprises a larger radius than the jaw/teeth line and is not parallel to them in order to maintain pressure against the inner part of the lips and cheeks pushing them outwards.

Figure 3A:
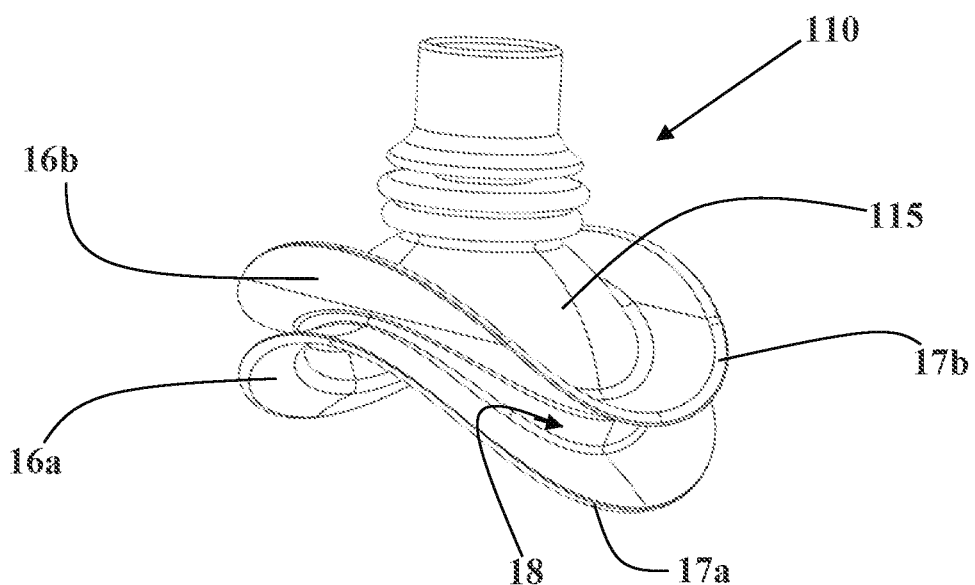
FIGS. 3A-3D illustrate a mouthpiece according to another embodiment of the present invention with two flanges.
Figure 3B:
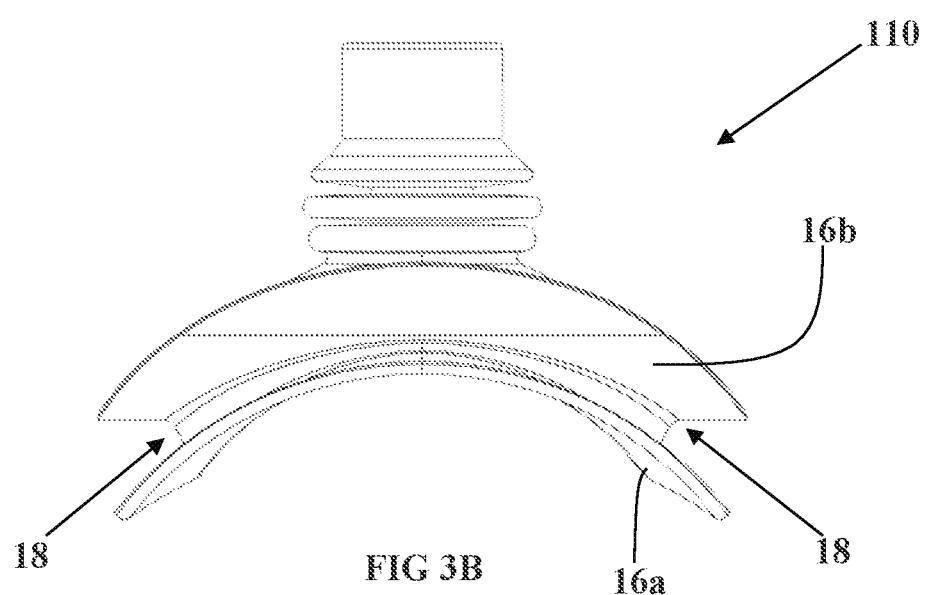
Figure 3C:
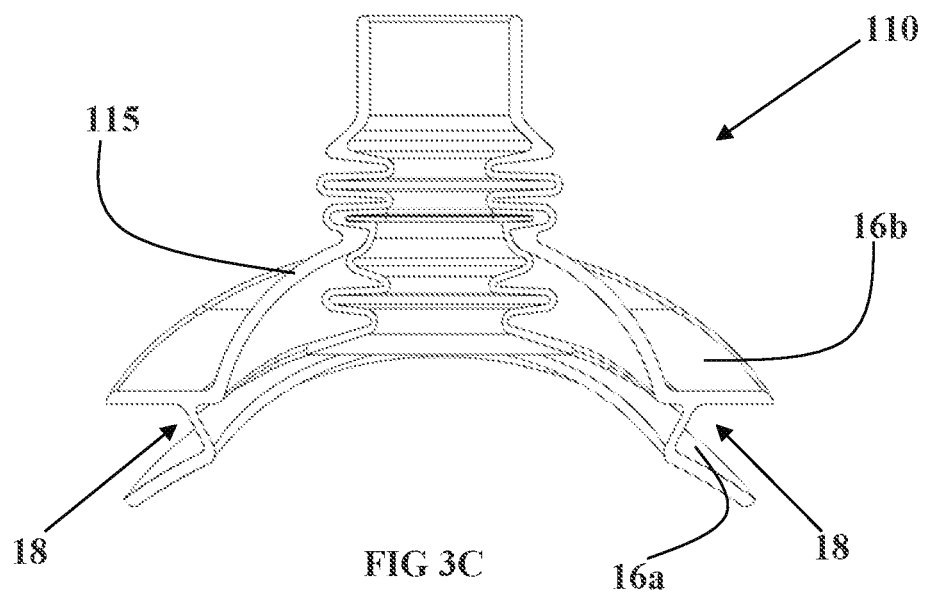
Figure 3D:
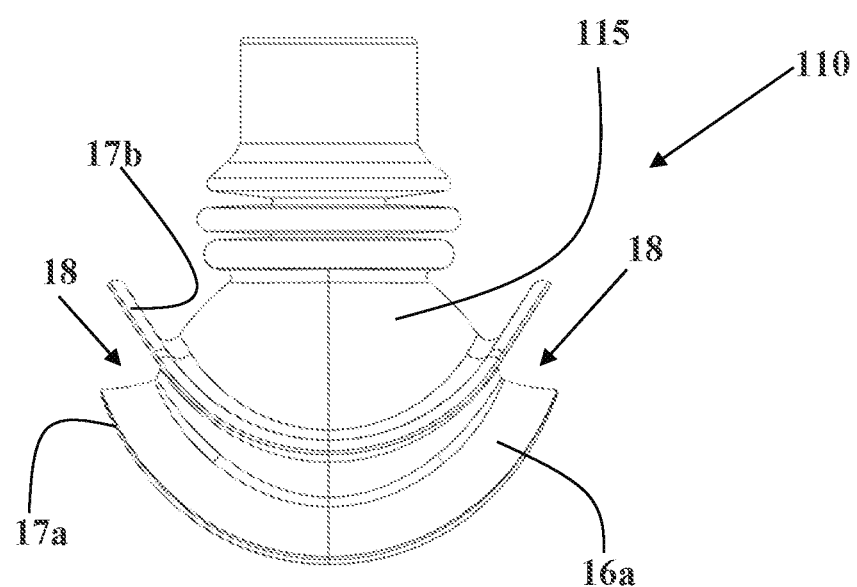
Figure 3E:
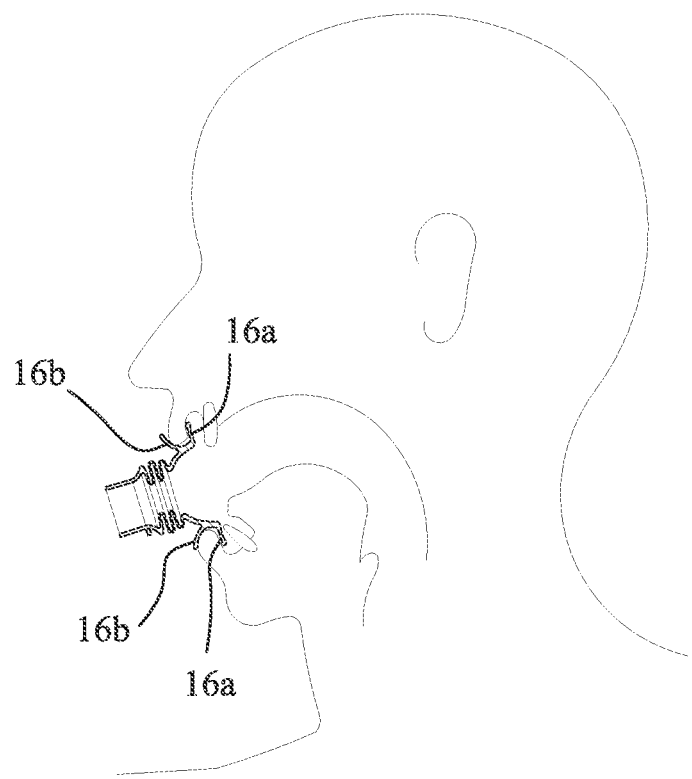
FIGS. 3E-3F are cross-sectional drawings of a user with the mouthpiece according to the embodiment of FIGS. 3A-3D.
Figure 3F:
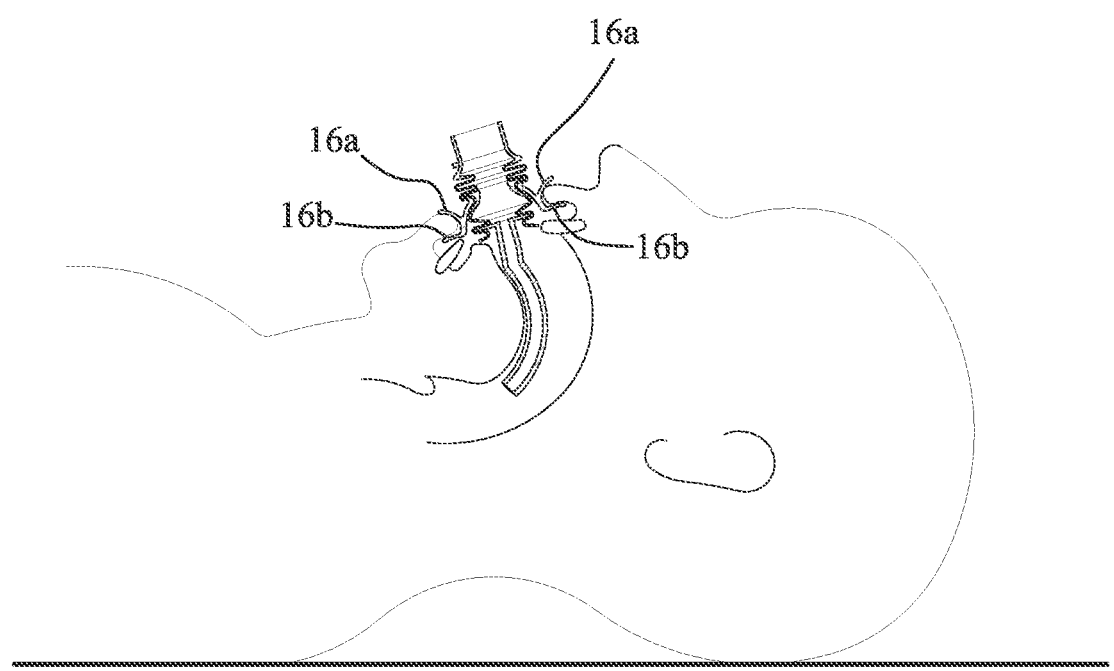
Figure 5A:
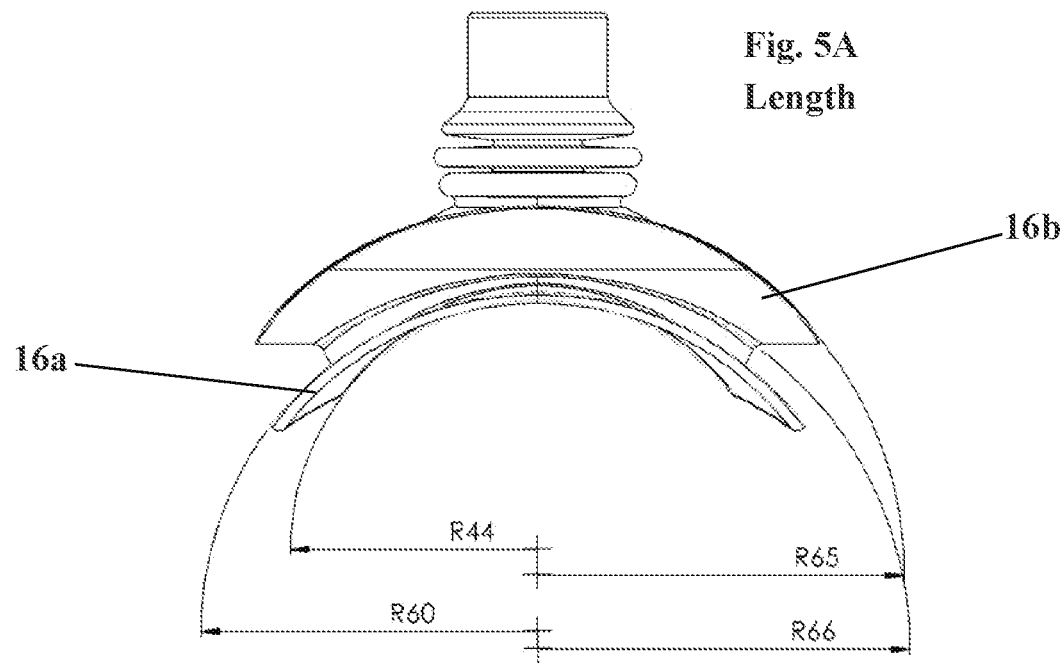
FIGS. 5A-5B illustrate a mouthpiece according to an embodiment of the present invention.
Figure 5B:
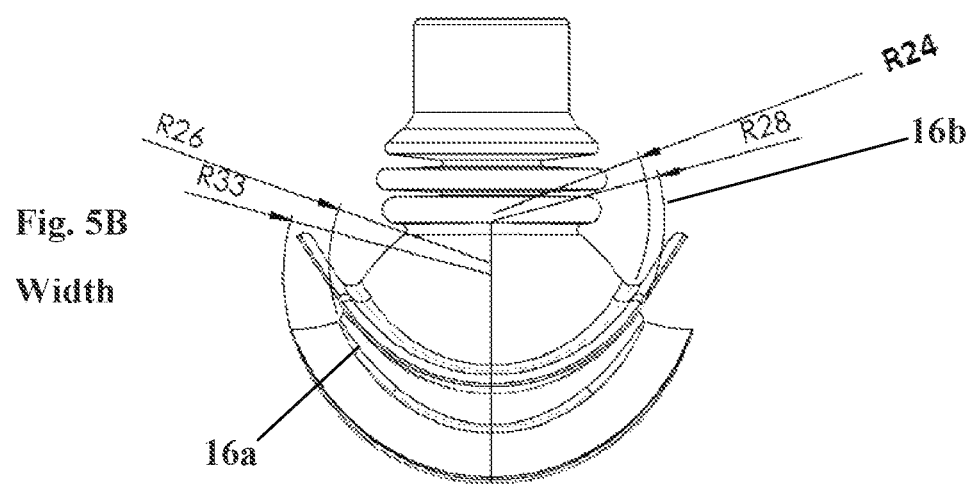

FIGS. 3E-3F are a cross-sectional drawings of a user with mouthpiece 110. According to one embodiment, flanges 16a and 16b are shaped in a manner that makes it easy to be inserted into the mouth. Preferably, the flanges 16a and 16b comprise an arc form along the longitude of the flanges and an arc form along the width of the flanges. FIGS. 5A-5B show an example of a cross section of the length and width respectively of a preferred embodiment accordingly.

Optionally flanges 16a and 16b comprise a bowed or saddle like shape. According to one specific embodiment, the proximal flange 16a distal side comprises a longitudinal arc form, the arc having a portion of the curvature properties of a circle with a radius usually between 40 mm-300 mm, and preferably 40 mm-75 mm, and more preferably 60 mm (shown in FIG. 5A). The proximal flange 16a proximal side comprises a longitudinal arc form, the arc having a portion of the curvature properties of a circle with a radius usually between 28 mm-300 mm, and preferably 28 mm-60 mm, and more preferably 44 mm (shown in FIG. 5A). The distal flange 16b distal side comprises a longitudinal arc form, the arc having a portion of the curvature properties of a circle with a radius usually between 50 mm-300 mm, and preferably 50 mm-80 mm, and more preferably 66 mm (shown in FIG. 5A). The distal flange 16b proximal side comprises a longitudinal arc form, the arc having a portion of the curvature properties of a circle with a radius usually between 50 mm-300 mm, and preferably 50 mm-75 mm, and more preferably 65 mm (shown in FIG. 5A).

The proximal flange 16a distal side comprises a transversely disposed arc form (at 90 degrees to the longitudinally disposed flanges shown in FIG. 5A), the arc having a portion of the curvature properties of a circle with a radius usually between 12 mm-250 mm, and preferably 12 mm-40 mm, and more preferably 26 mm (shown in FIG. 5B). The proximal flange 16a proximal side comprises a transversely disposed arc form, the arc having a portion of the curvature properties of a circle with a radius usually between 20 mm-250 mm, and preferably 20 mm-50 mm, and more preferably 33 mm (shown in FIG. 5B). The distal flange 16b distal side comprises a transversely disposed arc form, the arc having a portion of the curvature properties of a circle with a radius usually between 12 mm-250 mm, and preferably 12 mm-40 mm, and more preferably 24 mm (shown in FIG. 5B). The distal flange 16b proximal side comprises a transversely disposed arc form, the arc having a portion of the curvature properties of a circle with a radius usually between 15 mm-250 mm, and preferably 15 mm-45 mm, and more preferably 28 mm (shown in FIG. 5B). Optionally, the flanges can comprise a curve with a variable radius, or a curve that portions of it are completely straight.

The distance between the centers of the arcs of the proximal flange 16a is usually between 0 mm-20 mm, and preferably 15 mm. The distance between the centers of the arcs of the distal flange 16b is usually the same.

According to another embodiment, the flanges 16a and 16b are elliptic with a rectangular tendency. The width of the flange portion 16a (including portions 17a) is usually between 30 mm and 90 mm and preferably 64 mm. Its length is usually between 40 mm and 140 mm and preferably 95 mm. According to an embodiment, the width of the flange portion 16b (including portions 17b) is usually between 40 mm and 100 mm and preferably 64 mm. Its length is usually between 40 mm and 140 mm and preferably 100 mm. The distance between the flanges, i.e. the width of channel 18 is usually between 8 mm and 30 mm and preferably 14 mm.

The width of channel 18 (the distance between the flanges) can be the same all along it or can vary along the channel. According to one embodiment, it is usually between 25 mm and 70 mm and preferably 49 mm. Its length (the "bottom" of the channel surrounding the mouthpiece) is usually between 35 mm and 120 mm and preferably 71 mm. The channel 18 is suitable for various lips and prevents their movement and dislodging and maintains sealing even with the high pressure formed within the mouth.

The distal flange 16b is configured to provide additional support to prevent the movement of the lips and outbreak of the sealing obtained. When there is a blockage in one of the breathing organs and the air inflation causes an increased pressure within the mouth, the lips tend to expand and move outwardly. An increased pressure can also be caused in some cases by the exhalation of the patient. In these cases the distal flange 16b prevents the lips from moving outwardly and breaking the sealing.

According to an embodiment of the present invention a nose clamp is used during air inflation to prevent air leakage out of the nose. Preferably, the nose clamp is permanently attached to the mouthpiece in order to maintain a single-unit device. In this manner while treating a patient under field conditions, a healthcare provider pulls out the mouthpiece with the nose clamp attached automatically. The healthcare provider does not need to especially go out of his way to look for a nose clamp. This can save precious time.

The attachment between the nose clamp and mouthpiece is constructed in a way that one will not interfere with the other's functionality. In order for the functionality of the mouthpiece and the nose clamp not to collide and interrupt each other, they are separated in a manner such that they do not affect/move each other or affect the functionality of the other.

Figure 4A:
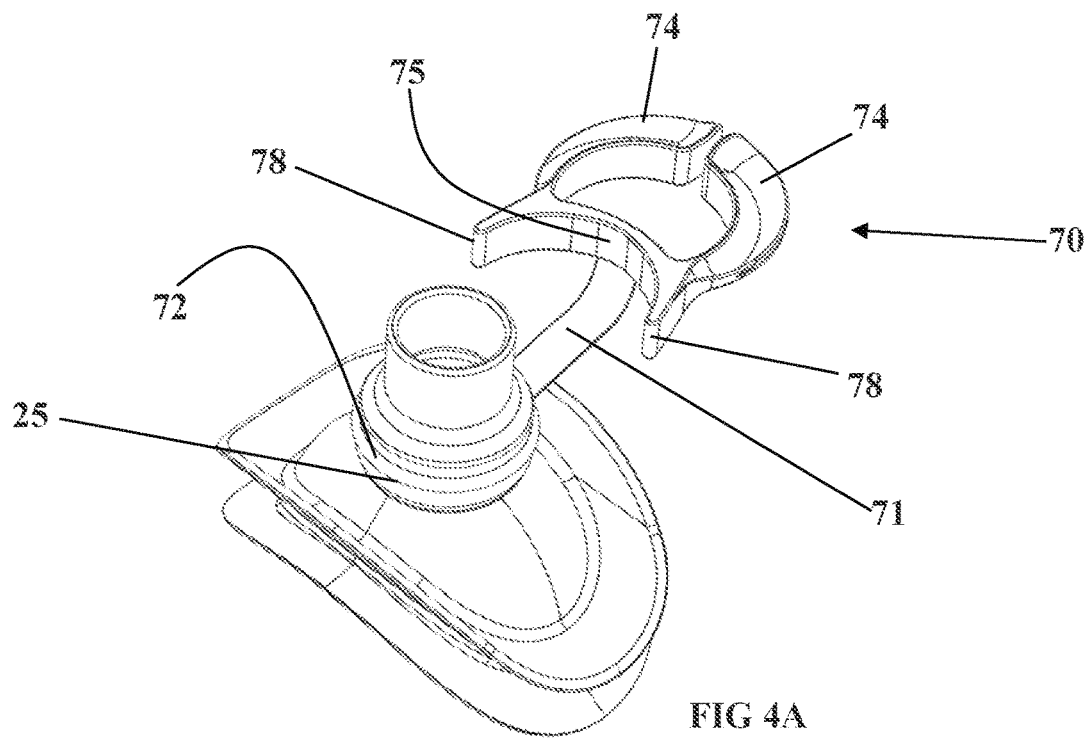
FIGS. 4A-4B illustrate a mouthpiece according to an embodiment of the present invention with a nose clamp.
Figure 4B:
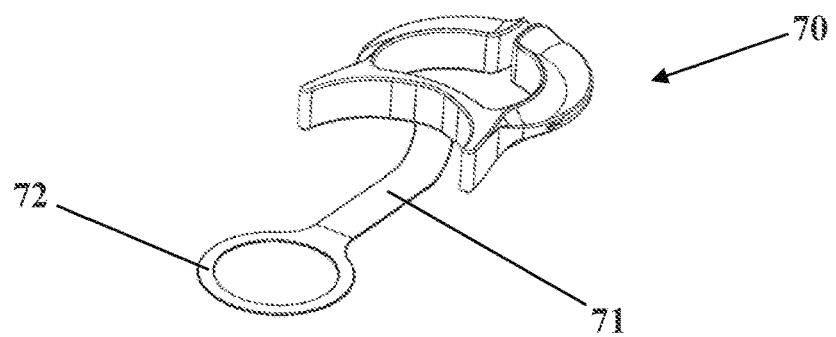
Figure 4B:
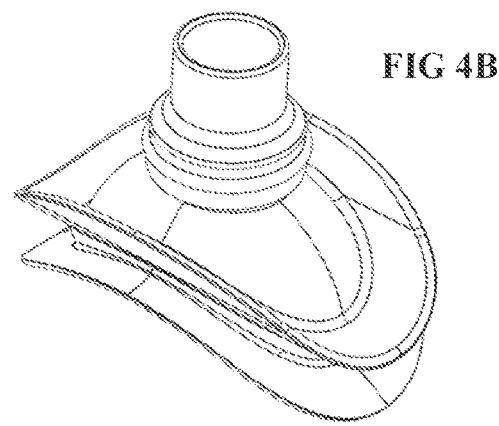

According to one embodiment of the present invention, a strap is attached to the nose clamp at one of its ends and to a portion of the mouthpiece (or tube connected thereto) at its other end. According to one embodiment (as shown in FIGS. 4a-4b), a strap 71 is connected at its first end to a nose clamp 70 wherein the strap 71 is connected at its other end to a ring portion 72 encircling the external narrow channel portion of corrugated portion 25. This causes a secure permanent connection between the mouthpiece and the nose clamp 70. The nose clamp 70 can be clipped to the distal end orifice of tube 20 and wrapped around tube 20. This enables an easy decouple of the nose clamp 70 when needed to be used.

According to an embodiment of the present invention, the nose clamp 70 comprises two flaps 74 and an adjustable reinforcement member 75 reinforcing the flaps against the nostrils, providing enough pressure to maintain nose sealing and prevent air from leaking/escaping through the nose without harming or injuring the nose tissues in a long term procedure. It is preferably comfortable to wear even on conscious people. The nose clamp 70 comprises two finger grips 78 (for the thumb and another finger), and the reinforcement member 75 allowing the opening of the flaps 74, and placing them on the nostrils, near the nose bone. The two finger grips 78 are attached to the two flaps 74 respectively and are attached to the reinforcement member 75 therebetween. The reinforcement member 75 comprises a spring force feature that tends to apply pressure on the flaps 74 pushing them one towards the other. When the medical personnel lets go of the finger grips 78 the flaps 74 each push towards each other and close the patient's nostrils.

The nose clamp 70 (without the strap) has a general length usually between 40 mm-80 mm, and preferably 62 mm. The nose clamp 70 has a general width usually between 20 mm-90 mm, and preferably 52 mm. The nose clamp 70 has a thickness usually between 5 mm-40 mm, and preferably 10 mm. Preferably, the nose clamp 70 and the reinforcement member 75 are comprised of material selected from the group consisting of nylon, polypropylen, polyethylen, abs, pvc or other plastics. Optionally, reinforcement member 75 is comprised of steel. This type of nose clamp allows the user to obtain a nose sealing in a fast, easy manner, which is possible with one hand.

According to another embodiment, the nose clamp 80 comprises two longitudinal arms 84 configured to be pressed along the nasal channels of the nose of a patient, and a reinforcement member 85 connected therebetween (FIGS. 6A-6E). The arms 84 may be substantially parallel to one another (e.g. FIG. 6B) or with a slight angle between them (e.g. FIG. 6C). The reinforcement member 85 comprises a spring force feature that tends to apply pressure on the arms 84 pushing them one towards the other, providing enough pressure to maintain nose sealing and prevent air from leaking/escaping through the nose without harming or injuring the nose tissues in the procedure.

The nose clamp 80 comprises two curved handles 88 extending distally from the edges of the arms 84. Optionally, the handles 88 curve such that the edges of the handles 88 are distally above the arms 84. Preferably the curved handles 88 have a "U" shape such that they comprise edge portions 88e that are substantially parallel to arms 84. The arms 84 or handles 88 may be straight or curved.

Figure 6D:
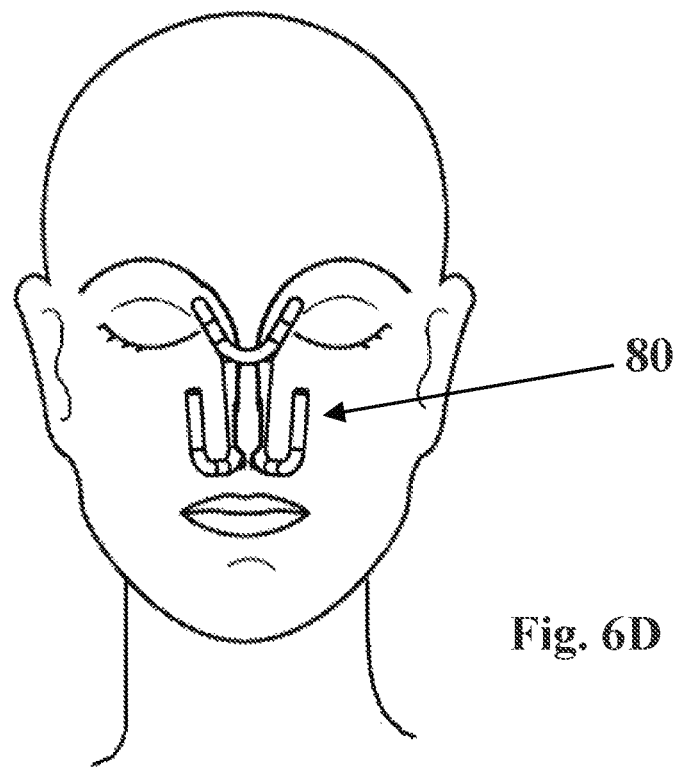

The reinforcement member 85 is connected to the edges of the arms 84 opposite to the edges connected to the handles 88. Preferably, the reinforcement member 85 is partially lifted and extends distally in relation to the plane of the arms 84 so not to contact the upper part of the nose and the eyes (as shown in FIG. 6D).

The nose clamp 80 is put on the patient by the user holding the handles 88 and separating them, thus causing separation of the arms 84 until being in position parallel to the nasal channels and then letting the handles 88 go, and thus the reinforcing member 85 applies pressure such that the arms 84 move one towards the other, being substantially parallel to and along the nasal channels and sealing the patient's nostrils. In order to release the nose clamp 80 the user holds the handles and moves them apart, thus moving the arms apart and releasing the nose clamp 80 from the nose.

According to a preferred embodiment, the whole nose clamp 80 is comprised of a winding tubular member forming the handles 88, arms 84 and reinforcing member 85 (as shown in FIGS. 6A-6E). The nose clamp 80 can be a continuous single unit (e.g. by casting) or combined by separate portions, connected by welding, sticking, gluing or other methods known in the art. The tubular member usually has a diameter of between 2-12 mm. The tubular member may be hollow or solid. The tubular member comprises a circular or elliptic cross section or combinations thereof. Portions of the tubular member cross-sections may have additional or less material in a manner such that it assists extraction from a pattern (in case manufactured by casting in a pattern). The arms 84 may comprise protrusions that assist sealing. Other portions such as the handles 88 may also comprise protrusions. The cross section may be unified or may vary along the nose clamp 80.

The arms 84 are usually in the range of 20-80 mm, and the distance between them in a rested state is usually between 1-20 mm.

According to one embodiment, the reinforcing member 85 is comprised of a combination of arc portions, preferably 1-8, having a diameter of preferably 4-40 mm. The arc combinations provide the appropriate spring pressure to push the arms 84 one towards the other. FIG. 6B show a nose clamp 80 with reinforcing member 85 comprising five arc portions 85a, 85b, 85c, 85d and 85e. FIG. 6C shows another form of reinforcing member 85 of nose clamp 80.

Preferably, the nose clamp 80 is comprised of material selected from the group consisting of the aforementioned plastics or other plastics. The nose clamp 80 of plastic may be manufactured by injection, heat bending, or combinations thereof. Optionally, nose clamp 80 is comprised of steel or other metals. Optionally, the arms 84 and/or the handles 88 (areas with skin contact) may be coated with soft silicon.

The soft coatings may be applied by dipping the nose clamp 80 into an appropriate material or inserted by threading, or other manners known in the art. The strap connecting the nose clamp 80 to the mouthpiece may be similar to the strap explained hereinabove. The strap may be comprised of plastic or fabric. The nose clamp 80 may be resistant such that it can be cleansed by autoclaving.

Figure 6E:
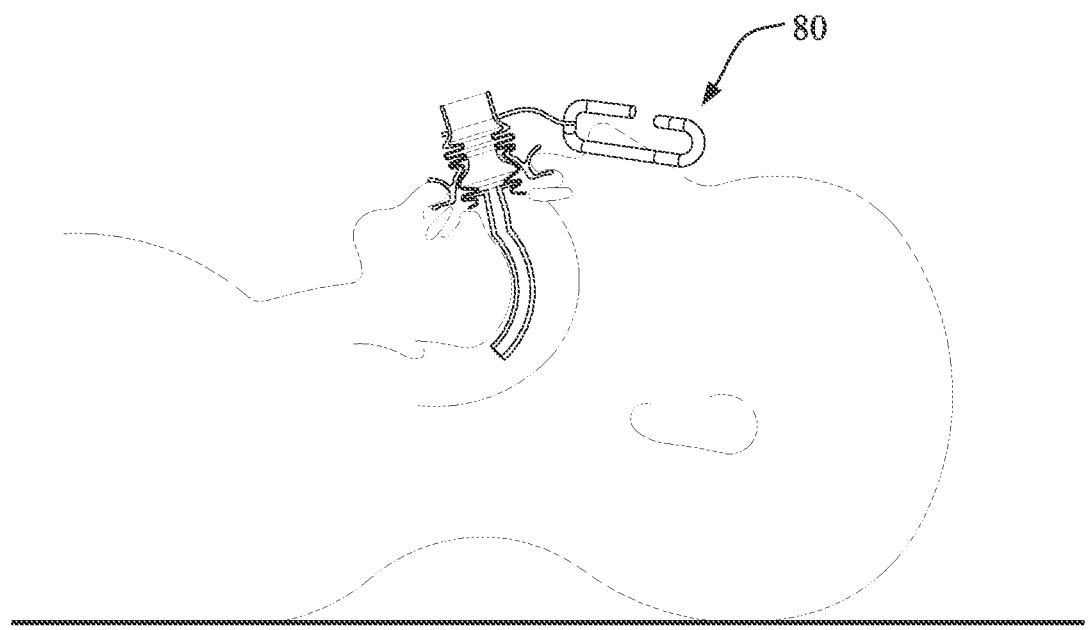

FIG. 6D shows a top view of nose clamp 80 applied on a patient. FIG. 6E shows a side view of nose clamp 80 (connected to the mouthpiece) applied on a patient. A preferred size of the nose clamp 80 may be applied on all nose sizes.

This embodiment (with the nose clamp) allows the user to obtain a nose sealing in a fast, easy manner. The placement of the mouthpiece and the nose clamp provide a fast and more important, efficient, long lasting, and user friendly solution, allowing the user to concentrate on providing airflow through the gas source to the mouth, as opposed to prior art solutions which require applying additional pressure (e.g. at nose, mouth) to maintain the sealing. The present invention enables a single healthcare provider to ventilate a person without becoming fatigued, and with no need for additional help (e.g. extra hand/component/element) or extra person.

The present invention also relates to a method for treating an unconscious patient (e.g. who is in cardiac arrest condition) or any condition that requires air inflation. The method comprises:
a) inserting the mouthpiece as described herein into a patient's mouth;
b) connecting the tube 20 to inflation means (e.g. bag valve resuscitator 26);
c) applying CPR using the inflation means.

According to one embodiment, the method (using the mouthpiece as described herein) comprises:
a) connecting the corrugated conduit 30 to an oropharyngeal airway flange 41;
b) inserting the oropharyngeal airway into the patient;
c) inserting and fitting the mouthpiece into a patient's mouth.
d) connecting the tube 20 to inflation means (e.g. bag valve resuscitator 26).
e) applying CPR with the inflation means.

While some of the embodiments of the invention have been described by way of illustration, it will be apparent that the invention can be carried into practice with many modifications, variations and adaptations, and with the use of numerous equivalents or alternative solutions that are within the scope of a person skilled in the art, without departing from the spirit of the invention, or the scope of the claims.

The invention claimed is:

1. A system for applying Cardiopulmonary Resuscitation (CPR) comprising:
an intraoral flexible mouthpiece comprising:
a hollow dome portion comprising a peripheral proximal edge and a distal portion, wherein said hollow dome portion has a peak and extends from said peripheral proximal edge to said distal portion, and wherein said hollow dome portion comprises a central orifice located at the distal portion of said hollow dome portion;
a peripheral flexible sheet flange attached along the entire dome portion peripheral proximal edge;
a tube attached to said central orifice and extending distally therefrom;
wherein said peripheral flexible sheet flange has a distal side and a proximal side and is configured to be placed in the mouth between the teeth and gums that engage the peripheral flexible sheet flange proximal side and the lips and cheeks that engage the peripheral flexible sheet flange distal side, wherein said peripheral flexible sheet flange is configured to be placed in a direction parallel to the teeth, wherein the dome shaped portion is configured to protrude outwardly in a distal direction out of the mouth;
wherein the peak of the dome portion is at the distal portion of said hollow dome portion and wherein said distal portion is a most distal portion of said dome portion; and
wherein the peripheral flexible sheet flange is in direct contact to the peripheral proximal edge; and
wherein said mouthpiece further comprises an internal flexible corrugated conduit having a distal end and a proximal end wherein said internal flexible corrugated conduit distal end is attached to the central orifice located at the distal portion of the hollow dome portion and extends proximally therefrom; and
an oropharyngeal airway comprising an airway flange, a main body portion and a proximal tip, wherein said airway flange is adapted to sealably connect to the internal flexible corrugated conduit.

2. The system of claim 1 wherein the tube is flexible.

3. The system of claim 1 wherein the tube comprises a resilient portion.

4. The system of claim 3 wherein the resilient portion is a corrugated portion.

5. The system of claim 1 wherein the peripheral flexible sheet flange comprises an edge surrounding said peripheral flexible sheet flange, wherein said peripheral flexible sheet flange edge is curved and/or comprises a thickened portion.

6. The system of claim 1 wherein the proximal end of the internal flexible corrugated conduit comprises a grip handle.

7. The system of claim 1 further comprising a distal flange configured to be placed distally to the lips, wherein said distal flange is attached surrounding a second peripheral portion of the dome portion that is distal to the proximal peripheral edge.

8. The system of claim 1 further comprising a nose clamp attached thereto.

9. The system of claim 8, wherein the tube comprises a resilient portion;
wherein the resilient portion is a corrugated portion;
and wherein said mouthpiece further comprises a strap connected at a first end to the nose clamp and at a second end to a ring portion configured to encircle the corrugated portion.

10. The system of claim 8 wherein the nose clamp comprises two flaps and a reinforcement member, wherein said reinforcement member comprises a spring force feature that applies pressure on said flaps pushing said flaps one towards the other.

11. The system of claim 10 further comprising two finger grips attached to the two flaps respectively, wherein said two finger grips are attached to the reinforcement member therebetween.

12. The system of claim 8 wherein the nose clamp comprises two longitudinal arms and a reinforcement member connected therebetween, wherein said reinforcement member comprises a spring force feature that applies pressure on said arms pushing said arms one towards the other.

13. The system of claim 12, wherein the nose clamp's two longitudinal arms comprise edges;
wherein the nose clamp comprises two curved handles extending distally from the nose clamp's two longitudinal arms' edges.

14. The system of claim 13, wherein the curved handles have a "U" shape comprising second edge portions that are substantially parallel to the arms.

15. The system of claim 1 further comprising:
a gas source coupled to the mouthpiece tube.

16. The system of claim 1 further comprising a gas source coupled to the mouthpiece tube.

17. The system of claim 1, wherein the peripheral flexible sheet flange is approximately perpendicular to the proximal peripheral edge of the dome shaped portion.

18. A method for treating an unconscious patient comprising:
a) inserting the system of claim 1 into a patient's mouth;
b) connecting the tube to a gas source;
c) applying CPR using the gas source.

19. A method for treating an unconscious patient comprising:
a) connecting the corrugated conduit of the system of claim 1 to the oropharyngeal airway flange;
b) inserting the oropharyngeal airway into the patient;
c) inserting and fitting said mouthpiece into a patient's mouth;
d) connecting the tube to a gas source; and
e) applying CPR using the gas source.

20. A system for applying Cardiopulmonary Resuscitation (CPR) comprising:
an intraoral flexible mouthpiece comprising:
a hollow dome portion comprising a peripheral proximal edge and a distal portion, wherein said hollow dome portion has a peak and extends from said peripheral proximal edge to said distal portion, and wherein said hollow dome portion comprises a central orifice located at the distal portion of said hollow dome portion;
a peripheral flexible sheet flange attached along the entire dome portion peripheral proximal edge;
a tube attached to said central orifice and extending distally therefrom;
wherein said peripheral flexible sheet flange has a distal side and a proximal side and is configured to be placed in the mouth between the teeth and gums that engage the peripheral flexible sheet flange proximal side and the lips and cheeks that engage the peripheral flexible sheet flange distal side, wherein said peripheral flexible sheet flange is configured to be placed in a direction parallel to the teeth, wherein the dome shaped portion is configured to protrude outwardly in a distal direction out of the mouth;
wherein the peak of the dome portion is at the distal portion of said hollow dome portion and wherein said distal portion is a most distal portion of said dome portion; and
wherein the peripheral flexible sheet flange is in direct contact to the peripheral proximal edge; and
wherein said mouthpiece further comprises a distal flange configured to be placed distally to the lips, wherein said distal flange is attached surrounding a second peripheral portion of the dome portion that is distal to the proximal peripheral edge such that a channel is formed on said dome portion, bounded by the peripheral flexible sheet flange, the distal flange and the dome portion that they are attached to; and
an oropharyngeal airway comprising an airway flange, a main body portion and a proximal tip, wherein said airway flange is adapted to sealably connect to an internal flexible corrugated conduit of the mouthpiece.

* * * * *